United States Patent [19]
Wong

[11] Patent Number: 5,587,143
[45] Date of Patent: Dec. 24, 1996

[54] BUTYLENE OXIDE-ETHYLENE OXIDE BLOCK COPOLYMER SURFACTANTS AS STABILIZER COATINGS FOR NANOPARTICLE COMPOSITIONS

[75] Inventor: Sui-Ming Wong, Collegeville, Pa.

[73] Assignee: NanoSystems L.L.C., Collegeville, Pa.

[21] Appl. No.: 267,082

[22] Filed: Jun. 28, 1994

[51] Int. Cl.$^6$ .......................... A61K 49/00; A61K 49/04
[52] U.S. Cl. .................. 424/9.1; 424/497; 424/9.455; 424/9.45
[58] Field of Search ................................ 424/78.31, 490, 424/497, 4.9; 514/772.3

[56] References Cited

U.S. PATENT DOCUMENTS

| | | | |
|---|---|---|---|
| 4,535,545 | 8/1985 | Sebag | 424/70.31 |
| 5,145,684 | 9/1992 | Liversidge et al. | |
| 5,318,767 | 6/1994 | Liversidge et al. | |
| 5,369,131 | 11/1994 | Poli et al. | 514/772.3 |
| 5,393,519 | 2/1995 | Dowell et al. | 424/70.31 |

OTHER PUBLICATIONS

U.S. pat. application Ser. No. 07/988,564 filed Dec. 10, 1992.
B–Series Polyglycols by Dow.

Primary Examiner—Peter F. Kulkosky
Attorney, Agent, or Firm—Rudman & Balogh

[57] ABSTRACT

This invention provides a composition comprised of nanoparticles containing a therapeutic or diagnostic agent having a nonionic polymeric surfactant as a surface modifier adsorbed on the surface thereof, the surfactant being a block copolymer of ethylene oxide and butylene oxide and a method of making such nanoparticles. The compositions exhibit reduced macrophage uptake and improved toxicological profiles and facilitate particle size reduction such that milling time can be reduced and/or sterile filtration of the nanoparticles can be accomplished.

8 Claims, No Drawings

– 5,587,143 –

BUTYLENE OXIDE-ETHYLENE OXIDE BLOCK COPOLYMER SURFACTANTS AS STABILIZER COATINGS FOR NANOPARTICLE COMPOSITIONS

FIELD OF THE INVENTION

This invention relates to therapeutic and diagnostic compositions containing a surfactant and to a method for the preparation thereof.

BACKGROUND OF THE INVENTION

U.S. Pat. No. 5,145,684 discloses particles of a drug substance having a surface modifier adsorbed on the surface thereof and methods for the preparation thereof by wet grinding. These particles have demonstrated significant pharmaceutical utility. Suitable surface modifiers described include various polymers. The preferred surface modifiers disclosed include Pluronic F68 and F108, which are block copolymers of ethylene oxide and propylene oxide, and Tetronic 908, which is a tetrafunctional block copolymer derived from sequential addition of ethylene oxide and propylene oxide to ethylene diamine.

U.S. Pat. No. 5,318,767 discloses x-ray contrast compositions comprising particles of an x-ray contrast agent having a surface modifier adsorbed on the surface thereof and methods for the preparation thereof by wet grinding. The above-noted surface modifiers are also disclosed as being useful therein. These x-ray contrast compositions have demonstrated remarkable utility in x-ray medical diagnostic imaging procedures.

P. Sarpotdar et al., U.S. patent application Ser. No. 07/988,564 filed Dec. 10, 1992, discloses therapeutic and diagnostic compositions with Olin-10 G, i.e., p-isononylphenoxypoly(glycidol) having improved autoclave stability.

However, some of the above-described polymeric surfactants have demonstrated less than superior toxicological profiles, for example, in a "smudge cell" assay. In addition, these prior art surfactant coatings, on some occasions, have exhibited less than desirable inhibition of macrophage uptake.

Furthermore, sterilization of therapeutic and diagnostic agents in nanoparticulate form stabilized by a surface modifier is difficult. Filtration using a filter of 0.22 μm mesh size is sufficient to remove most bacteria and viruses, but the nanoparticles, due to their sizes, cannot be sterile filtered without accounting for substantial drug losses.

Moreover, the wet grinding methods described in the patents noted above often entail grinding for days or even weeks which can be undesirable, e.g., from the standpoint of process scale-up.

Consequently, it would be highly desirable to provide surfactant coatings for nanoparticles which reduce the smudge cell effect, inhibit macrophage uptake and facilitate particle size reduction such that milling time can be reduced and/or sterile filtration of the nanoparticles can be accomplished without substantial particle losses.

SUMMARY OF THE INVENTION

We have discovered surfactant coatings for nanoparticles which reduce the smudge cell effect, inhibit macrophage uptake and unexpectedly facilitate particle size reduction.

More specifically, in accordance with this invention, there is provided a composition comprised of nanoparticles containing a therapeutic or diagnostic agent having a nonionic polymeric surfactant as a surface modifier adsorbed on the surface thereof, wherein said surfactant is a block copolymer of ethylene oxide and butylene oxide.

It is an advantageous feature of this invention that surfactants are provided for nanoparticle compositions which exhibit a reduced smudge cell effect.

It is another advantageous feature of this invention that nanoparticle compositions are provided which inhibit macrophage uptake.

Yet another advantageous feature of this invention is that nanoparticle compositions are provided in a narrow particle size distribution.

Still another advantageous feature of this invention is that a surfactant coating is provided for nanoparticles which facilitates particle size reduction, thus reducing milling time and potentially enabling sterile filtration of the nanoparticles to be accomplished without substantial particle losses.

These and other advantages will become readily apparent upon reference to the following description of preferred embodiments.

DESCRIPTION OF PREFERRED EMBODIMENTS

This invention is described hereinafter primarily in connection with nanoparticles containing a therapeutic or diagnostic agent having a nonionic block copolymer of ethylene oxide and butylene oxide as a surface modifier adsorbed on the surface thereof. In addition, the invention is believed to be useful in composition with nanoparticles containing, e.g., photographic and cosmetic agents, and with other nonionic polymeric surface modifiers containing blocks of ethylene oxide and other hydrophobes such as pentylene oxide, hexylene oxide, cyclohexylene oxide and styrene oxide.

Surfactants useful herein are nonionic block copolymers. Preferred surfactants contain at least one polyethylene oxide (PEO) block as the hydrophilic portion of the molecule and at least one polybutylene oxide (PBO) block as the hydrophobic portion of the surfactant. Particularly preferred surfactants are diblock, triblock, and higher block copolymers of ethylene oxide and butylene oxide, such as are represented, for example, by the following structural formula: —(PEO)—(PBO)—; —(PEO)—(PBO)—(PEO)—; and —(PEO)—(PBO)—(PEO)—(PBO)—. Highly preferred surfactants include triblock copolymers of the structure —(PEO)—(PBO)—(PEO)—having molecular weights of 3800 and 5000 which are commercially available from Dow Chemical, Midland, Mich., and are hereinafter referred to as B20-3800 and B20-5000. These surfactants contain about 80% by weight PEO.

In a preferred embodiment, the surfactant is a triblock polymer having the structure:

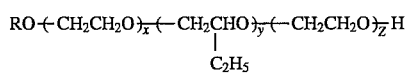

wherein R is H or an active hydrogen group, such as alkyl, aryl, carboxyalkyl or carboxyaryl, x is 15–700, y is 5–200 and z is 15–700. In particularly preferred embodiments, the surfactant has a molecular weight of 1,000–50,000, preferably 2,000–40,000 and more preferably 3,000–30,000. In preferred embodiments, the polymer comprises at least about 50%, and more preferably at least 60% by weight ethylene oxide units. The reason for this is that the presence of a major weight proportion of hydrophilic units confers aqueous solubility to the polymer.

While applicants do not wish to be bound by theoretical mechanisms, it is believed that the presence of the butylene oxide hydrophobe in the polymer chain increases lipophilic interaction between surfactant and the hydrophobic therapeutic or diagnostic agent, thus facilitating the ability of the surfactant to coat the surface of the particulate therapeutic or diagnostic agent.

These surface modifiers are commercially available and/or can be prepared by techniques known in the art.

The nanoparticles useful in the practice of this invention can be prepared according to the methods disclosed in U.S. Pat. No. 5,145,684 and U.S. Pat. No. 5,318,767.

Briefly, a method for the preparation of a nanoparticle composition according to this invention includes the steps of introducing a diagnostic or therapeutic agent, a liquid medium, grinding media, and optionally, a surface modifier into a grinding vessel; wet grinding to reduce the particle size of the agent to less than about 1000 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions.

A general procedure for preparing the particles useful in the practice of this invention follows. The therapeutic or diagnostic agent selected is obtained commercially and/or prepared by techniques known in the art, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60% and preferably is from 5–30% (w/w). It is preferred, but not essential, that the surface modifier be present in the premix. The concentration of the surface modifier can vary from about 0.1 to 90%, and preferably is 1–75%, more preferably 2–50% and most preferably 5–45% by weight based on the total combined weight of the drug substance and surface modifier. The apparent viscosity of the premix suspension is preferably less than about 1000 centipoise.

The premix can be used directly by wet grinding to reduce the average particle size in the dispersion to less than about 1000 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, a planetary mill and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, media with higher density, e.g., glass (2.6 $g/cm^3$), zirconium silicate (3.7 $g/cm^3$), and zirconium oxide (5.4 $g/cm^3$), are generally preferred for more efficient milling. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful. In addition, polymeric media having a density typically from 1 to 2 $g/cm^3$ are also expected to be useful under certain milling conditions. The grinding media can be a polymeric media such as described in European Patent Application No. 600,528.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 $kg/cm^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 2–50%, and most preferably 5–45% by weight based on the total weight of the dry particle. The surface modifier preferably is present in an amount exceeding the critical miscelle concentration.

Therapeutic and diagnostic agents useful in the composition of the present invention include those disclosed in U.S. Pat. Nos. 5,145,684, and 5,318,767 whose disclosures are incorporated herein by reference. Preferred diagnostic agents include the x-ray imaging agent ethyl 3,5-diacetamido-2,4,6-triiodobenzoate, (compound A); 6-ethoxy-6-oxohexyl-3, 5-bis(acetamido)-2,4,6-triiodobenzoate (compound B); ethyl-2-(3,5-bis(acetamido)-2,4,6-triiodobenzoyloxy) butyrate; ethyl diatrizoxyacetate; ethyl 2-(3,5-bis(acetamido)-2,4,6-triiodobenzoyloxy)propionate; N-ethyl 2-(3,5-bis(acetamido)-2,4,6-triiodobenzoyloxy)acetamide; isopropyl 2-(3,5-bis(acetamido)-2,4,6-triiodobenzoyloxy) acetamide; diethyl 2-(3,5-bis(acetamido)-2,4,6-triiodobenzoyloxy) malonate; and ethyl 2-(3,5-bis(acetamido)-2,4,6-triiodobenzoyloxy) phenylacetate.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 1000 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method can be carried out under aseptic conditions. Thereafter, the nanoparticle composition preferably is subjected to a sterilization process.

As noted elsewhere herein, sterile filtration will not provide adequate sterilization for nanoparticles without causing significant loss of active material. Although the compositions of this invention can be sterile filtered, other methods of sterilization can also be employed. For example, steam or moist heat sterilization at temperatures of about 121° C. for a time period of about 20 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

In preferred embodiments, the therapeutic or diagnostic agent in the form of surface modified nanoparticles can be associated with a cloud point modifier to enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the nanoparticle composition.

Therapeutic and diagnostic compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step administering to the mammal in need of treatment an effective amount of the above-described therapeutic composition. The selected dosage level of the therapeutic substance for treatment is effective to obtain a desired therapeutic response for a particular composition and method of administration. The selected dosage level therefore, depends upon the particular drug substance, the desired therapeutic effect, on the route of administration, on the desired duration of treatment and other factors.

In a preferred embodiment, the diagnostic compound is an x-ray contrast agent, such as an iodinated x-ray contrast agent. Thus, the diagnostic compositions of this invention include an x-ray contrast composition comprising particles containing an x-ray contrast agent and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast compositions can comprise from about 1–99.9, preferably 2–45 and more preferably 10–30% by weight of the above-described particles, the remainder of the composition being the carrier, additives and the like. Compositions up to about 100% by weight of the particles are contemplated when the composition is in a lyophilized form.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined.

Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like. In addition to preferred applications, i.e., for blood pool, liver, spleen and lymph node imaging, the x-ray contrast compositions of this invention are also expected to be useful as an angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

This invention further relates to a method of making nanoparticles having a nonionic block copolymer of ethylene oxide and butylene oxide adsorbed on the surface thereof, comprised of contacting said diagnostic or therapeutic agent with a block copolymer of ethylene oxide and butylene oxide for a time and under conditions sufficient to form a stabilized nanoparticle. Contacting can be by admixing a suspension of the diagnostic or therapeutic agent with a solution of the block copolymer such as described above.

The following examples further illustrate the invention.

EXAMPLES 1–4 AND COMPARATIVE EXAMPLES A–D

The following formulations were prepared at 15% diagnostic agent and 4% surfactant (w/v). A 6% stock solution was prepared by dissolving 600 mg B20-3800 or B20-5000 surfactants in 10 ml deionized water. To each 15 ml amber colored bottle, 7.5 ml ZrSi beads of size 1.1 mm, 562 mg of Compound A or Compound B, 2.5 ml of 6% stock surfactant solution and 0.994 ml deionized water were added. The sample bottle was sealed and placed on a roller mill running at 160 rpm for 5 days. At day 5, aliquot of samples were diluted 50 fold with deionized water for particle size measurement by photon correlation spectroscopy (PCS).

| Example | Core | Surfactant | Mean Particle Size (nm) |
|---|---|---|---|
| 1 | Compound A | B20-5000 | 106 |
| 2 | Compound A | B20-3800 | 110 |
| A | Compound A | F108 | 130 |
| B | Compound A | T908 | 241 |
| 3 | Compound B | B20-5000 | 102 |
| 4 | Compound B | B20-3800 | 94 |
| C | Compound B | F108 | 140 |
| D | Compound B | T908 | 144 |

This data demonstrates that the ethylene oxide-butylene oxide surfactant resulted in unexpectedly reduced mean particle size compared to F108 and T908 when milled with two different x-ray contrast agent cores, i.e., ethyl 3,5-diacetoamido-2,4,6-triiodobenzoate and 6-ethoxy-6-oxohexyl-3,5-bis(acetamido)-2,4,6-triiodobenzoate, under identical milling conditions.

In addition, tail vein injection of a 2% solution of B20-5000 at 0.05 ml/mice (n=3) and 0.5 ml/mice (n=3) was well tolerated by mice.

B20-3800 was tested in a smudge cell assay according to the following procedure. This technique has been developed in order to evaluate the in vitro effect of surfactant on the lymphocytes in whole blood. Into each well of a round bottom 96 well microtiter plate is pipetted 225 µl of whole human blood and 25 µl of surfactant solution at the desired concentration. The plate is placed on a blood rocker for two hours at room temperature to incubate the surfactant/blood mixture. After incubation, a small drop of the surfactant/blood mixture is placed on a glass slide and a wedge-prep blood smear is made on the slide. The smears are air dried, and contacted with ethanol to fix the smear, and subsequently stained with Wright-Giemsa stain, available from Sigma Chemical. Lymphocytes with damaged or broken cell membranes which appear on the slide as smudge cells are counted as a percentage of the total leukocytes seen. An average smudge cell count greater than 15 is considered a statistically significant positive smudge cell effect. B20-3800 was evaluated in the above-described smudge cell assay at concentrations of 10, 1 and 0.001% (v/v). Control A contained sterile water (no surfactant) and Control B contained 1% T908. The test results were as follows:

| Sample | Average Smudge Cell Count | Average Intact Lymphocyte Count |
|---|---|---|
| Control A (no surfactant) | 1.5 | 26.5 |
| Control B T908 (1%) | 19.0 | 9.0 |
| B20-3800 (10%) | 2.5 | 23.0 |
| B20-3800 (1%) | 6.0 | 21.5 |
| B20-3800 (0.001%) | 8.0 | 16.0 |

The data show that B20-3800 exhibited a significantly lower average smudge cell count and a higher average intact lymphocyte count compared to the T908 control even at a 10 times greater concentration.

B20-5000 coated on polystyrene particles also significantly inhibited the phagocytosis of such particles by macrophages while B20-3800 demonstrated a less dramatic effect. The ability of surfactant coated polystyrene particles to inhibit macrophage uptake was tested according to the procedure described by E. Liversidge et al in "Direct Suppression of Phagocytosis by Amphiphatic Polymer Surfactants", *Pharm. Res.*; Vol. 9, No. 9, pp. 1177–83. The number of particles measured per cell for B20-5000 surfactant coated polystyrene particles was about 3,000; about 28,000 for B20-3800 surfactant coated particles, and about 47,000 for the naked polystyrene particle control. In other words, B20-5000 exhibited about a 95% reduction in macrophage uptake compared to control and the B20-3800 exhibited about a 40% reduction.

EXAMPLES 5–6

In a procedure similar to that described in Examples 1–4 above, Danazol was milled in conjunction with B20-5000 and B20-3800. The mean particle size measured by PCS was 196 nm and 189 nm, respectively.

The invention has been described in detail with particular reference to certain preferred embodiments thereof, but it will be understood that variations and modifications can be effected within the spirit and scope of the invention.

I claim:

1. A composition comprised of nanoparticles containing a therapeutic or diagnostic agent having a nonionic polymeric surfactant as a surface modifier adsorbed on the surface thereof, wherein said surfactant is a triblock copolymer having the structure

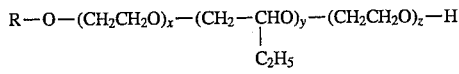

wherein
R is H,
x and y are 15–200, and
z is 5–200; and
said polymer has a molecular weight of 3,000–5,000 and comprises at least 60% by weight of ethylene oxide units.

2. A method of making nanoparticles containing a diagnostic or therapeutic agent having a nonionic block copolymer of ethylene oxide and butylene oxide adsorbed on the surface thereof comprised on contacting said diagnostic or therapeutic agent with a block copolymer of ethylene oxide and butylene oxide for a time and under conditions sufficient to form a stabilized nanoparticle, wherein said block copolymer of ethylene oxide and butylene oxide is a triblock copolymer having the structure

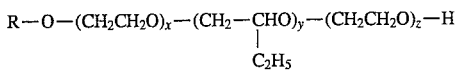

wherein
R is H,
x and y are 15–200, and
z is 5–200; and
said polymer has a molecular weight of 3,000–5,000 and comprises at least 60% by weight of ethylene oxide units.

3. The composition of claim 1 wherein the molecular weight of the copolymer is about 5000.

4. The composition of claim 3 wherein the agent is a therapeutic agent.

5. The composition of claim 2 wherein the molecular weight of the copolymer is about 5000.

6. The method of claim 5 wherein the agent is a therapeutic agent.

7. A composition comprised of nanoparticles of danazol having a nonionic polymeric surfactant as a surface modifier adsorbed on the surface thereof, wherein said surfactant is a triblock copolymer having the structure

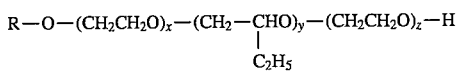

wherein
R is H,
x and y are 15–200, and
z is 5–200; and
said polymer has a molecular weight of 3,000–5,000 and comprises at least 60% by weight of ethylene oxide units.

8. The composition of claim 3 wherein said therapeutic agent is Danazol.

* * * * *